United States Patent [19]

Hofmeister et al.

[11] 4,016,269
[45] Apr. 5, 1977

[54] 17α-HYDROXY-1,3,5(10),15-ESTRATETRAENES AND PROCESS FOR THEIR PRODUCTION

[75] Inventors: Helmut Hofmeister; Klaus Annen; Rudolf Wiechert; Henry Laurent, all of Berlin, Germany

[73] Assignee: Schering Aktiengesellschaft, Berlin & Bergkamen, Germany

[22] Filed: Aug. 11, 1975

[21] Appl. No.: 603,773

[30] Foreign Application Priority Data

Aug. 12, 1974 Germany ............ 2439082

[52] U.S. Cl. .................. 424/241; 260/239.55 R; 260/397.4; 260/397.5; 424/243
[51] Int. Cl.² .................. A61K 31/58
[58] Field of Search .... /Machine Searched Steroids; 260/239.55 R, 397.5 A

[56] References Cited
UNITED STATES PATENTS

| | | | |
|---|---|---|---|
| 3,079,408 | 2/1973 | Mueller | 260/397.4 |
| 3,433,785 | 3/1969 | Manson et al. | 260/239.5 |
| 3,501,509 | 3/1970 | Kuo et al. | 260/397.5 |

Primary Examiner—Elbert L. Roberts
Attorney, Agent, or Firm—Millen & White

[57] ABSTRACT

Novel estrogenic 17α-hydroxy-1,3,5(10),15-estratetraenes of the formula

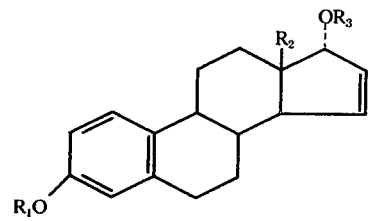

wherein $R_1$ is H, lower alkyl or lower acyl, $R_2$ is lower alkyl and $R_3$ is H, lower alkyl, lower acyl or tetrahydropyranyloxy, are produced by (a) reacting a 16α,17α-epoxy-estratriene with lithium halide or HCl in glacial acetic acid; converting the resulting halohydrin into a 16-halo-17-tetrahydropyranyl ether; and splitting off hydrogen halide from therefrom; or (b) reacting the 16α,17α-epoxy-estratriene with diphenylselenide and alkali metal borohydride; oxidizing the thus-produced 17α-hydroxy-16β-phenylselenide to the corresponding phenylselenide oxide; and forming the $\Delta^{15}$ double bond by heating with removal of phenyl—Se—OH.

15 Claims, No Drawings

17α-HYDROXY-1,3,5(10),15-ESTRATETRAENES AND PROCESS FOR THEIR PRODUCTION

BACKGROUND OF THE INVENTION

It is known from German Unexamined Laid-Open Application DOS No. 2,207,421 that 15α,16α-methylene-4-estren-17β-ols possess valuable properties. Depending on the alkyl group in the 17a-position, they are hormones having pronounced androgenic or progestational activity.

These compounds are produced from 17α-hydroxy-$\Delta^{15}$-steroids of the pregnane series by methylation according to Simmons-Smith (J. Am. Chem. Soc. 80 [1958] 5323).

The pregnane side chain in the 17α-position is merely an auxiliary function for the introduction of the 17α-hydroxy-$\Delta^{15}$-structure and for introducing the methylene group. After the methylenation, the side chain in the 17β-position must be broken off again. The building and later removal of the 17β-side chain render the conventional process complicated and uneconomical.

It is an object of the invention to provide novel steroids having a 17α-hydroxy-$\Delta^{15}$-structure which do not contain a substituent in the 17β-position. It is another object to provide a novel method for the production of novel 17α-hydroxy-$\Delta^{15}$-steroids of the estrane series. Other objects will be apparent to those skilled in the art.

SUMMARY OF THE INVENTION

In a composition aspect, this invention relates to 17α-hydroxy-1,3,5(10),15-estratetraenes of the general formula

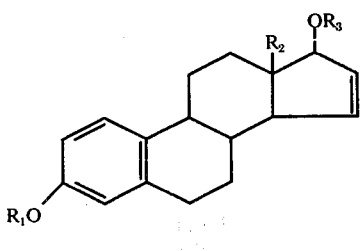

wherein $R_1$ is a hydrogen atom, lower alkyl or lower acyl; $R_2$ is lower alkyl and $R_3$ is a hydrogen atom, lower alkyl, lower acyl or an oxygen-containing, saturated heterocyclic residue.

In another composition aspect, this invention relates to novel intermediates for the production thereof. In a further composition aspect, this invention relates to pharmaceutical compositions comprising a novel $\Delta^{15}$-estratetraene of this invention in admixture with a pharmaceutically acceptable carrier.

In process aspects, this invention relates to processes for the production and use of the novel compounds of this invention.

DETAILED DISCUSSION

Examples of $R_1$, $R_2$ and $R_3$ lower alkyl groups are alkyl of 1–5 carbon atoms, preferably methyl and ethyl.

Examples of $R_1$ and $R_3$ lower acyl groups are the physiologically acceptable acyl groups of acids conventionally employed for the esterification of steroid alcohols. Preferred acyl groups are alkanoyl of 1–5 carbon atoms, e.g., formic acid, acetic acid, propionic acid, butyric acid, isobutyric acid, valeric acid and isovaleric acid. Although alkanoyl of 1–5 carbon atoms are preferred, $R_1$ and $R_3$ acyl groups contemplated equivalents are those of the above formula wherein $R_1$ and $R_2$ each are the acyl group of another organic acid, e.g., a carboxylic acid containing up to 15 carbon atoms, especially an aliphatic carboxylic acid, e.g., an alkanoic acid of 6–12 carbon atoms, which can be unsaturated, branched, polybasic, or substituted in the usual manner, for example, by hydroxy or halogen atoms; a cycloaliphatic, aromatic and mixed aromatic-aliphatic (alkaryl and aralkyl) acid, which can be likewise be substituted in the usual manner, examples of preferred such equivalent acids being caproic acid, enanthic acid, undecyclic acid, oleic acid, dichloroacetic acid, cyclopentylpropionic acid, phenylpropionic acid, phenylacetic acid, phenoxyacetic acid, succinic acid, benzoic acid; others being acids containing 1–18, preferably 2–12 carbon atoms, including an aliphatic acid containing 1–18, preferably 1–6 carbon atoms, e.g., α-ethylvaleric, 2-ethylbutyric, 3-ethylbutyric, hexanoic, diethylacetic, triethylacetic, enanthic, octanoic, undecyclic and palmitic acid; a cyclic acid, preferably a cycloaliphatic acid, containing, e.g., 5–18 carbon atoms, e.g., cyclopropylideneacetic, cyclobutylcarboxylic, cyclopentylcarboxylic, cyclopentylacetic, cyclohexylacetic, cyclohexylacetic and β-cyclohexylpropionic acid; a carbocyclic aryl or alkaryl acid, e.g., containing 6–18 carbon atoms, and 1 to 5, preferably 1 or 2 rings, e.g., benzoic, 2-, 3-, or 4-methylbenzoic, 2,3-, 2,4-, 2,5-, 2,6-, 3,4- and 3,5-dimethylbenzoic, ethylbenzoic, 2,3,6-trimethylbenzoic and 3-methyl-α-naphthoic acid; an aralkyl acid, e.g., containing 7 to 18 carbon atoms, e.g., β-phenylpropionic, a polybasic acid, e.g., containing 2–18 carbon atoms and 1 to 5 hydroxy groups, e.g., glycolic, lactic, citric, tartaric, d-maleic, d-glyceric, and salicyclic acid; and the corresponding acids containing one, two or more of simple substituents, e.g., halo, alkoxy, acyloxy, etc., in the molecule, e.g., chloroacetic, fluoroacetic, trichloroacetic, trifluoroacetic, 2,3,4-trimethoxybenzoic, phenoxyacetic, α-naphthoxyacetic acid.

An oxygen-containing, saturated heterocyclic $R_3$ group is one derived from a heterocycle with at least one oxygen atom in the ring and which is perhydrogenated in the oxygen-containing ring. Of these, tetrahydrofuryl and tetrahydropyranyl and especially tetrahydropyranyl, are preferred.

The novel compounds of general Formula I possess estrogenic activity and are useful as intermediates in the production of further steroids. For example, compounds of Formula I wherein $R_3$ is a hydrogen atom can be converted in a simple manner to the 15α,16α-methylene-4-estrene-17β-ols known from DOS Nos. 2,207,421 by methylene group introduction, Birch reduction, oxidation to the 17-ketone, and addition in the 17-position, which reactions will be explained in greater detail with reference to the following formula scheme:

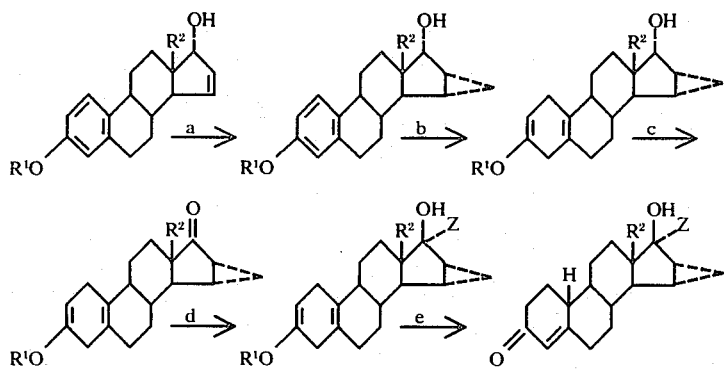

In the above formulae, $R^1$ = alkyl; $R^2$ = alkyl; and $Z$ = hydrogen, alkyl, alkenyl or alkinyl.

The introduction of the methylene group according to reaction (a) takes place according to Simmons-Smith with methylene iodide and zinc/silver. By a Birch reduction (b) with alkali metal, especially lithium, in liquid ammonia, the 3-enol ether is obtained, which can be oxidized (c) to the 17-ketone with the pyridine-$SO_3$-complex. By reduction (d) of the 17-keto group with conventional reducing agents or by reaction with an organometallic compound ("Z" metal) and by enol ether splitting (e), the therapeutically valuable $15\alpha,1-6\alpha$-methylene-4-estrene-$17\beta$-ols are obtained. The organometallic compound ("Z" metal) can be an alkyl magnesium halide, e.g., methylmagnesium bromide or iodide, an alkenyl magnesium and/or alkenyl zinc halide, e.g., vinyl- or allylmagnesium bromide, or an alkinyl magnesium halide, e.g., ethinyl- or propinylmagnesium bromide, or an alkali metal acetylide, e.g., potassium acetylide.

The novel method of synthesis via the $17\alpha$-hydroxy-1,3,5(10),15-estratetraenes of Formula I offers the advantage that it is no longer necessary to proceed through compounds of the pregnane series. Since the compounds must be produced by a total synthesis method, and estranes are first formed during such a total synthesis, the conventional path via the pregnanes represents a detour in the synthesis.

In a process aspect, this invention relates to a process for the production of the novel $17\alpha$-hydroxy-1,3,5(10),15-estratetraenes of general Formula I, which comprises the steps of reacting a $16\alpha,17\alpha$-epoxy-estratriene of the general Formula II

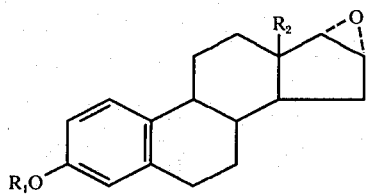

wherein $R_1$ and $R_2$ have the values given above, a. with lithium halide or HCl in glacial acetic acid converting the thus-produced halohydrin into the corresponding 17-tetrahydropyranyl ether of general Formula III:

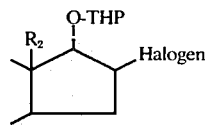

introducing the $\Delta^{15}$-double bond by heating with an alkaline reagent while splitting off hydrogen halide; and optionally thereafter splitting off tetrahydropyranyl ether group; or b. with diphenyldiselenide and alkali metal borohydride; oxidizing the thus-produced $17\alpha$-hydroxy-$16\beta$-phenylselenide to the corresponding selenium oxide of general Formula IV:

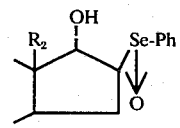

and introducing the $\Delta^{15}$-double bond by heating the thus-produced selenium oxide while splitting off Ph-Se-OH; or c. with lithium salt of a strong base;

and, depending on the desired final value for $R_1$ and $R_3$, free hydroxy groups are optionally thereafter esterified or etherified and/or ether or acyl groups are split off.

According to method (a), a $16\alpha,17\alpha$-epoxy-estratriene of general Formula II is first reacted with lithium halide in glacial acetic acid or with hydrogen chloride in glacial acetic acid. Simply allowing the reaction solution to stand at room temperature is sufficient to accomplish this reaction, with reaction times of 1–3 hours being normally adequate. Especially suitable as the lithium halide are lithium chloride and bromide.

The $16\beta,17\alpha$-halohydrin obtained during this reaction is then converted in the usual manner into the corresponding 17-tetrahydropyranyl ether, which is accomplished most advantageously with dihydropyan in the presence of an acid at room temperature. Suitable acids are, for example, phosphorus oxychloride, hydrochloric acid, and p-toluenesulfonic acid. Hydrogen halide is split off from the $16\beta$-halogen compound with masked (blocked) $17\alpha$-hydroxy group by heating in an alkaline reagent. Suitable alkaline reagents are, for example, alkali metal alkoxides of 1–6 carbon atoms, e.g., potassium tert-butylate in dimethyl sulfoxide or 1,5-diazabicyclo [5,4,0]undecene-5, or other base capable of reacting with hydrogen halide under anhydrous conditions. The heating step is preferably effected at temperatures of 60°–180° C, more preferably 70°–150° C. Operating under nitrogen has proven to be advantageous, particularly at the higher temperatures. The splitting off of hydrogen halide is usually complete after about 15–50 hours. It is surprising that the splitting off of hydrogen halide leads to a $\Delta^{15}$-double bond, rather than to the $\Delta^{16}$-double bond, because a secondary hydrogen atom is split off from the 15-position, whereas a tertiary hydrogen atom is present in the 17-position.

The subsequent splitting of the tetrahydropyranyl ether, as an optional measure, is conducted as customary with a weak acid in the presence of water.

According to method (b), a 16α,17α-epoxy-estratriene of general Formula II is reacted with diphenyldiselenide and an alkali metal borohydride. The reaction is preferably conducted in an alcoholic solution, e.g., in ethanol, at the boiling temperature. The thus-obtained 17α-hydroxy-16β-phenylselenide is subsequently oxidized to the corresponding selenium oxide.

Suitable oxidizing agents are, for example, hydrogen peroxide, alkali periodates, and peracids, e.g., perbenzoic acid, m-chloroperbenzoic acid, p-nitroperbenzoic acid, monoperphthalic acid, etc. By heating to temperatures of about 40°–80° C, the $\Delta^{15}$-double bond is introduced while splitting off Ph—Se—OH. Method (b) can be conducted in a single operating step (one-pot process).

The formation of allyl alcohols from epoxides with diphenyldiselenide has been described by K. B. Sharpless et al, J. Am. Chem. Soc. 95 (1973) 2697. This reaction, however, has heretofore not been utilized for opening a 16α,17α-epoxy steroid. It is surprising that the reaction of diphenyldiselenide and NaBH$_4$ with five-ring epoxides take place analogously to the reactions on six-ring epoxides, since many reactions in connection with five-ring compounds differ from those conducted on six-ring compounds.

According to method (C), a 16α,17α-epoxy-estratriene of general Formula II is converted in one reaction stage into the estratetraene of general Formula I, using a lithium salt of a strong base. Suitable lithium salts of strong bases are, for example, n-butyllithium, tert.-butyllithium, and lithium tetramethylpiperidine. The reaction is preferably carried out in an ether, especially an aliphatic ether such as diethyl ether, or in a hydrocarbon, such as benzene, pentane, hexane and cyclohexane at temperatures from about −20° to +50° C.

For the subsequent esterification, etherification and/or splitting of the esters or ethers, those processes conventional in the steroid chemistry can be employed. The esterification of the 3- and/or 17-hydroxy group is preferably conducted with an acid anhydride in the presence of a tertiary amine.

The saponification of an ester is accomplished preferably in an alcoholic solution with a weak base, e.g., potassium carbonate. To etherify the phenolic 3-hydroxy group, diazoalkanes, especially diazomethane can be utilized. The etherification of the 17-hydroxy group is preferably conducted with dialkyl sulfates in the presence of bases, such as potassium hydroxide, or with alkyl halides in dimethyl sulfoxide in the presence of bases, such as sodium hydride. The last two methods also make possible the etherification of the 3- and 17-hydroxy groups in one operating step. Another etherifying reagent for the 17-hydroxy group is dihydropyran.

The phenol ether splitting in the 3-position can preferably be accomplished with boron tribromide in methylene chloride at low temperatures, e.g., about −10° to +5° C.

The splitting of tetrahydropyranyl ethers in the 17-position takes place under gentle conditions at room temperature while adding a weak, aqueous acid, such as oxalic acid.

The compounds of Formula I possess pharmacological activity, particularly estrogenic activity. They are useful for the treatment of females in the postmenopausal period, e.g., climacteric and its sequelae.

This invention thus also relates to pharmaceutical compositions comprising an estratetraene of general Formula I in admixture with a pharmaceutical carrier.

Such compositions are produced in the usual manner by formulating the effective agents into the desired forms of application, e.g., tablets, dragees, capsules, oral and injectable solutions, employing the usual vehicles, diluents, flavorameliorating agents, etc. customary in galenic pharmacy.

The effective agent concentrations in the thusformulated drugs is dependent on the mode of administration. Thus, a tablet preferably contains 0.01– 10 mg; solutions for parenteral administration preferably contain 0.1 – 20 mg/ml of solution.

As will be apparent to those skilled in the art, the dosage of the medicinal agents of this invention can vary with the type of administration and the respectively selected compound. Moreover, the dosage can vary from patient to patient. In general, the compounds of the present invention are administered at a dosage level which can achieve the desired results without causing any disadvantageous or deleterious side effects. Thus, the compounds are administered, for example, at a dosage level ranging from approximately 0.02 mg to about 20 mg, although modifications can be made under certain circumstances, so that a dosage level of more or less than this range can be employed.

The compounds of general Formula I are also useful as intermediates for the production of the corresponding D-ring saturated estrogens, e.g., by hydrogenating at low pressure, e.g., ambient to 15 psi g, with hydrogen in the presence of a noble metal hydrogenation catalyst, e.g., platinum oxide or palladium or charcoal.

The 18-methyl compounds of general Formula II used as the starting materials can be prepared as follows:

A:
16α,17α-Epoxy-3-methoxy-18-methyl-1,3,5(10)-estratriene 3.0 g. of 3-methoxy-18-methyl-1,3,5(10)-estratrien-17-one [G. Greenspan et al., J. Org. Chem. 31, 2512 (1966)] is agitated in 200 ml. of methanol with 3.6g. of p-toluenesulfonic acid hydrazide while adding 0.1 ml. of concentrated sulfuric acid for 6 hours at 70° C. The solution is gradually cooled and then allowed to stand in an ice bath for several hours. The crystallized product is vacuum-filtered and recrystallized from acetone/hexane.

Yield: 3.3 g. of 3-methoxy-18-methyl-17-tosylhydrazono-1,3,5(10)-estratriene, m.p. 215° C. $[\alpha]_D^{20}=$ +54°.

38.4 g. of 3-methoxy-18-methyl-17-tosylhydrazono-1,3,5(10)-estratriene, suspended in 800 ml. of absolute ether, is combined under stirring dropwise with 158ml. of a 1.2N ether methyllithium solution. The reaction solution is agitated, after the methyllithium solution has been added, for another hour at room temperature, then diluted with ethyl acetate, and washed neutral with 2N HCl solution and water. The crude product is chromatographed on silica gel with acetone/hexane [gradient 0-5% acetone/hexane]. Yeild: 21.6 g. of 3-methoxy-18-methyl-1,3,5(10),16-estratetraene as an oily product. $[\alpha]_D^{20} = +113°$.

60 g. of 3-methoxy-18-methyl-1,3,5(10),16-estratetraene in 2.1. of ethylene chloride is gradually combined at room temperature with a solution of 46 g. of p-nitroperbenzoic acid in 250 ml. of tert.-butanol and 50 ml. of ethylene chloride. After 18 hours, the reaction mixture is diluted with ethyl acetate and washed successively several times with sodium thiosulfate solution and water. Chromatography of the crude product on silica gel with 4–5% acetone/hexane yields 56.0 g. of 16α,17α-epoxy-3-methoxy-18-methyl-1,3,5(10)-estratriene, m.p. 96°–97° C.; $[\alpha]_D^{20} = +84°$.

B:
16α,17α-Epoxy-3-hydroxy-18-methyl-1,3,5(10)-estratriene 500 mg. of 3-methoxy-18-methyl-1,3,5(10),16-estratetraene is combined under nitrogen in 20 ml. of methylene chloride with 5 ml. of boron tribromide at −5° C. while agitating the reaction mixture. The latter is agitated for 20 hours at −5° C., then poured on ice water, and the organic extracts are washed neutral with water. The crude product is purified by preparative layer chromatography (eluent: hexane/ethyl acetate = 7 : 3). Yield: 310 mg. of 3-hydroxy-18-methyl-1,3,5(10),16-estratetraene as an oily product.

At room temperature, a solution of 360 mg. of p-nitroperbenzoic acid in 2.5 ml. of tert.-butanol and 0.5 ml. of ethylene chloride is gradually added to 450 mg. of 3-hydroxy-18-methyl-1,3,5(10),16-estratetraene in 15 ml. of ethylene chloride. After 18 hours, the crude product is worked up as described in (A) and purified by preparative layer chromatography (eluent: hexane/ethyl acetate = 7 : 3). In this way, 310 mg. of 16α,17α-epoxy-3-hydroxy-18-methyl-1,3,5(10)-estratriene is isolated as an oily product.

C:
3-Acetoxy-16α,17α-epoxy-18-methyl-1,3,5(10)-estratriene 300 mg. of 3-hydroxy-18-methyl-1,3,5(10),16-estratetraene is stirred in 3 ml. of pyridine with 0.9 ml. of acetic anhydride for 2 hours at room temperature. The solution is introduced into ice water. The precipitate is vacuum-filtered, washed with water, dissolved in methylene chloride, and dried over sodium sulfate. The crude product is purified by preparative layer chromatography (eluent: hexane/ethyl acetate = 7 : 3). Yield: 255 mg. of 3-acetoxy-18 -methyl-1,3,5(10),16-estratetraene is isolated as an oily product.

At room temperature, a solution of 460 mg. of p-nitroperbenzoic acid in 3 ml. of tert.-butanol and 0.6 ml. of ethylene chloride is gradually added to 600 mg. of 3-acetoxy-18-methyl-1,3,5(10),16-estratetraene in 20 ml. of ethylene chloride. After 18 hours, the crude product is worked up as described in (A) and purified by preparative layer chromatography (eluent: hexane/ethyl acetate = 7 : 3). In this way, 490mg. of 3-acetoxy-16α,17α-epoxy-18-methyl-1,3,5(10)-estratriene is isolated as an oily product.

D:
3-Ethoxy-16α,17α-epoxy-18-methyl-1,3,5(10)-estratriene

Under agitation and at room temperature, 600 mg. of 3-hydroxy-18-methyl-1,3,5(10),16-estratetraene in 5 ml. of hexamethylphosphoric triamide is combined with 1 ml. of aqueous sodium hydroxide solution (25% strength). After 30 minutes, 1.5 ml. of ethyl iodide is slowly added thereto dropwise, and the solution is introduced into ice water after a reaction time of 3 hours. The mixture is then extracted with methylene chloride, and the organic phase is washed with 5% hydrochloric acid and water so that it becomes neutral. The crude product is purified by preparative layer chromatography (eluent: hexane/ethyl acetate = 7 : 3), thus obtaining 510 mg. of 3-ethoxy-18-methyl-1,3,5(10),16-estratetraene as an oily product.

At room temperature, a solution of 400 mg. of p-nitroperbenzoic acid in 2.5 ml. of tert.-butanol and 0.5 ml. of ethylene chloride is added gradually to 55 mg. of 3-ethoxy-18-methyl-1,3,5(10),16-estratetraene in 15 ml. of ethylene chloride. After 18 hours, the crude product is worked up as set forth in (A) and purified by preparative layer chromatography (eluent: hexane/ethyl acetate =7 : 3), thus isolating 380 mg. of 3-ethoxy-16α, 17α-epoxy-18-methyl-1,3,5(10)-estratriene as an oily product.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 2.0 g. of 16α,17α-epoxy-3-methoxy-18-methyl-1,3,5(10)-estratriene is stirred at room temperature in 10 ml. of glacial acetic acid with 2 g. of lithium bromide. After 2 hours, the solution is introduced into ice water. The thusprecipitated product is vacuum-filtered, washed with water, and dissolved in methylene chloride. Chromatography of the crude product on silica gel with 5.5 – 7.5% acetone/hexane yields 1.5g. of 16β-bromo-3-methoxy-18-methyl-1,3,5(10)-estratrien-17α-ol as an oily product. $[\alpha]_D^{20} = +35.2°$.

b. 6.0 g. of 16β-bromo-3-methoxy-18-methyl-1,3,5(10)-estratrien-17α-ol is reacted in 60 ml. of absolute tetrahydrofuran with 12 ml. of distilled dihydropyran while adding 0.1 ml. of distilled phosphorus oxychloride at room temperature. After 18 hours, the solution is diluted with methylene chloride, neutralized with sodium bicarbonate solution, and washed repeatedly with water. The crude product is chromatographed on silica gel with acetone/hexane (gradient 0–5% acetone/hexane). Yield: 6.4 g. of 16β-bromo-3-methoxy-18-methyl-17α-tetrahydropyranyloxy-1,3,5(10)-estratriene as an oily product. $[\alpha]_D^{20} = +35.6°$.

c. 3.5 g. of 16β-bromo-3-methoxy-18-methyl-17α-tetrahydropyranyloxy-1,3,5(10)-estratriene is agitated in 15 ml. of 1,5-diazabicyclo[5,4,0]undecene-5 (DBU) for 44 hours at 140° C. under nitrogen. The solution is diluted, after cooling, with ethyl acetate and washed successively several times with 2N HCl and water. The crude 3-methoxy-18-methyl-17α-tetrahydropyranyloxy-1,3,5(10),15-estratetraene (2.9 g.) is stirred in 105 ml. of methanol with 700 mg. of oxalic acid for 24 hours under nitrogen at room temperature. The solution is neutralized with sodium bicarbonate solution and concentrated under vacuum. The residue is taken up in methylene chloride, washed with water, and dried. Chromatography on silica gel with 8–12% acetone/hexane yields 1.1 g. of 3-methoxy-18-methyl-1,3,5(10),15-estratetraen-17α-ol as an oily product. $[\alpha]_D^{20} = -97.2°$.

d. 1.0 g. of 16β-bromo-3-methoxy-18-methyl-17α-tetrahydropyranyloxy-1,3,5(10)-estratriene is agitated in 20 ml. of dimethyl sulfoxide with 3 g. of potassium tert.-butylate for 16 hours at 80° C. The reaction mixture is introduced into ice water. The precipitate is vacuum-filtered, washed with water, dissolved in methylene chloride, and dried over sodium sulfate. The crude product is purified by preparative layer chromatography (eluent: hexane/ethyl acetate =7 : 3). Yield: 300 mg. of 3-methoxy-18-methyl-17α-tetrahydropyranyloxy-1,3,5-(10),15-estratetraene is isolated as an oily product. $[\alpha]_D^{20} = -88°$.

EXAMPLE 2

3.7 g. of diphenyldiselenide is dissolved in 200 ml. of absolute ethanol and combined at room temperature with 1.0 g. of sodium borohydride. After the yellow solution has lost its color, 5.0 g. of 16α,17α-epoxy-3-methoxy-18-methyl-1,3,5(10)-estratriene is added thereto and the mixture is heated under reflux for 30 hours. The solution is then cooled to 0° C. Dropwise, 11ml. of 30% $H_2O_2$ is added to the reaction solution and the latter is then gradually heated to 50° C. After 2 hours, the solution is introduced into ice water. The precipitate is vacuum-filtered, washed with water, and taken up in methylene chloride. After chromatography on silica gel with 6–8% acetone/hexane, 1.9 g. of 3-methoxy-18-methyl-1,3,5(10),15-estratetraen-17α-ol is obtained as an oily product. $[\alpha]_D^{20} = -108°$.

EXAMPLE 3

1.9 g. of diphenyldiselenide is dissolved in 100 ml. of absolute ethanol and combined at room temperature with 500 mg. of sodium borohydride. After decolorization of the yellow solution, 2.5 g. of 16α,17α-epoxy-3-methoxy-1,3,5(10)-estratriene [B. Schoenecker et al., Z.Chem [Chemical News] 10 (6), (1910)] is added thereto, and the mixture is heated for 27 hours under reflux. After cooling to 0° C., 6 ml. of 30% $H_2O_2$ is added dropwise thereto, and the solution is gradually warmed to 50° C. After 2 hours, the solution is poured into ice water. The thus-precipitated product is vacuum-filtered, washed with water, taken up in methylene chloride, and dried over sodium sulfate. After the crude product has been chromatographed on silica gel with 5 – 7.5% acetone/hexane, 1.1 g. of 3-methoxy-1,3,5(10),15-estratetraen-17α-ol is isolated as an oily product.

EXAMPLE 4

300 mg. of 3-methoxy-18-methyl-1,3,5(10),15-estratetraen-17α-ol is stirred in 3 ml. of pyridine with 0.5 ml. of acetic anhydride for 5 hours at room temperature. The solution is introduced into ice water. The precipitate is vacuum-filtered, washed with water, dissolved in methylene chloride, and dried over sodium sulfate. The crude product is purified by preparative layer chromatography (eluent: acetone/hexane = 7 : 3).

Yield: 230 mg. of 17α-acetoxy-3-methoxy-18-methyl-1,3,5(10),15-estratetraene as an oily product. $[\alpha]_D^{20} = -92°$.

EXAMPLE 5

200 mg. of 3-methoxy-1,3,5(10),15-estratetraen-17α-ol is agitated for 3 hours in 2.5 ml. of pyridine with 0.5 ml. of acetic anhydride. After the product has been worked up as described in Example 4 and purified by preparative layer chromatography (eluent: hexane/ethyl acetate = 7 : 3), 170 mg. of 17α-acetoxy-3-methoxy-1,3,5(10),15-estratetraene is isolated as an oily product.

EXAMPLE 6

400 mg. of 3-methoxy-1,3,5(10),15-estratetraen-17α-ol is agitated at room temperature in 4 ml. of absolute tetrahydrofuran with 1.5 ml. of distilled dihydropyran while adding one drop of phosphorus oxychloride. After 5 hours, the solution is diluted with methylene chloride, neutralized with sodium bicarbonate solution, and washed repeatedly with water. The crude product is purified by preparative layer chromatography (eluent: hexane/ethyl acetate = 7 : 3). Yield: 280 mg. of 3-methoxy-17α-tetrahydropyranyloxy-1,3,5(10),15-estratetraene as an oily product.

EXAMPLE 7

1.7 g. of diphenyldiselenide is dissolved in 90 ml. of absolute ethanol and mixed at room temperature with 480 mg. of sodium borohydride. After decolorization of the yellow solution, 2.2 g. of 3-acetoxy-16α,17α-epoxy-1,3,5(10)-estratriene [V. Prelog et al., Helv. 28, 250 (1945)] is added thereto and the mixture heated for 20 hours under reflux. After cooling to 0° C., 5 ml. of 30% $H_2O_2$ is added dropwise, and the solution is gradually warmed to 50° C. The product is worked up in accordance with Example 3, and then an after-acetylation is carried out in 5 ml. of pyridine with 2.5 ml. of acetic anhydride. The reaction solution is introduced into ice water. The thusprecipitated product is vacuum-filtered, washed with water, dissolved in methylene chloride, and dried over sodium sulfate. By chromatography of the crude product on silica gel with acetone/hexane, 930 mg. of 3-acetoxy-1,3,5(10),15-estratetraen-17α-ol is obtained.

EXAMPLE 8

380 mg. of 3-acetoxy-1,3,5(10),15-estratetraen-17α-ol is stirred for 4 hours at room temperature in 5 ml. of methanol and 1 ml of water with 300 mg. of potassium carbonate. The reaction solution is filtered off from the insoluble matter, neutralized with glacial acetic acid, concentrated under vacuum, and the residue is taken up in methylene chloride. After purification by preparative layer chromatography (eluent: hexane/ethyl acetate = 7 : 3), 112 mg. of 1,3,5(10),-15-estratetraene-3,17α-diol is obtained as an oily product.

EXAMPLE 9

Under argon and at room temperature, 10 ml. of a 2-molar tert.-butyllithium solution in pentane is added dropwise to 600 mg. of 16α,17α-epoxy-3-methoxy-18-methyl-1,3,5(10)-estratriene in 60 ml. of cyclohexane. After 4 hours, the solution is gently combined with water, washed neutral, and dried over sodium sulfate. Purification of the crude product by preparative layer chromatography (system: hexane/ethyl acetate = 7 : 3)

yields 270 mg. of 3-methoxy-18-methyl-1,3,5(10),15-estratetraen-17α-ol as an oil. $[\alpha]_D^{20} = =103°$.

EXAMPLE 10

Under argon and at room temperature, 16 ml. of a 20% n-butyllithium solution in hexane is added dropwise to 1.1 g. of 16α,17α-epoxy-3-methoxy-18-methyl-1,3,5(10)-estratriene in 100 ml. of cyclohexane. After 6 hours, the solution is combined with water, washed neutral, and dried over sodium sulfate. Chromatography of the crude product on silica gel with 7-9% acetone/hexane yields 290 mg. of 3-methoxy-18-methyl-1,3,5(10),15-estratetraen-17α-ol as an oily product. $[\alpha]_D^{20} = -105°$.

EXAMPLE 11

380 mg. of 16α,17α-epoxy-3-methoxy-18-methyl-1,3,5(10)-estratriene in 10 ml. of benzene is combined at room temperature under argon with 3 ml. of a 2-molar tert.-butyllithium solution in pentane. The solution is diluted with benzene after 2.5 hours, mixed with water, washed neutral, and dried over sodium sulfate. After purifying the crude product by preparative layer chromatography (system: hexane/ethyl acetate = 7 : 3), the yield is 120 mg. of 3-methoxy-18-methyl-1,3,5(10),15-estratetraen-17α-ol in the form of an oil. $[\alpha]_D^{20} = -107°$.

EXAMPLE 12

At 0° C. and under argon, 4 ml. of a 2-molar tert.-butyllithium solution in pentane is added to 450 mg. of 16α,17α-epoxy-3-methoxy-18-methyl-1,3,5(10)-estratriene in 12 ml. of ether. After 1 hour, the solution is diluted with ether, gently mixed with water, washed neutral, and dried over sodium sulfate. After purifying the crude product by preparative layer chromatography (system: hexane/ethyl acetate = 7 : 3), 140 mg. of 3-methoxy-18-methyl-1,3,5(10),15-estratetraen-17α-ol is obtained as an oily product. $[\alpha]_D^{20} = -105°$.

The following description contains directions for the further processing of the compounds of general Formula I of this invention to the final products according to DOS No. 2,207,421, using as an example the preparation of 17α-ethinyl-17α-hydroxy-18-methyl-15α,16α-methylene-4-estren-3-one:

8.5 g. of 3-methoxy-18-methyl-1,3,5(10),15-estratetraen-17α-ol in 200 ml. of absolute ether and 200 ml. of ethylene glycol dimethyl ether is combined with 32 g. of zinc-silver. Under agitation and refluxing, 30 ml. of methylene iodide is gradually added dropwise to this mixture. After 5 hours, the reaction mixture is cooled to room temperature, diluted with ether, and filtered off from the insoluble matter. The filtrate is washed several times successively with concentrated ammonium chloride solution and water. After chromatography of the crude product on silica gel with 11-13% acetone/hexane, 4.5 g. of 3-methoxy-18-methyl-15α,16α-methylene-1,3,5(10)-estratrien-17α-ol is obtained as an oily product. $[\alpha]_D^{20} = +11°$.

1.0 g. of 3-methoxy-18-methyl-15α,16α-methylene-1,3,5(10)-estratrien-17α-ol is dissolved in 30 ml. of absolute ether and added dropwise to 60 ml. of liquid ammonia. Then, at −75° C., 1.0 g. of lithium is added thereto within 15 minutes under agitation. After 30 minutes, 20 ml. of ethanol is slowly dropped thereto and the ammonia is allowed to evaporate. The residue is taken up in ether, washed neutral with water, and dried over sodium sulfate, yielding 1.0 g. of crude 3-methoxy-18-methyl-15α,16α-methylene-2,5(10)-estradien-17α-ol.

At 15° C. under agitation, a solution of 2.0 g. of pyridine-SO₃ complex in 10 ml. of dimethyl sulfoxide is added dropwise to 900 mg. of crude 3-methoxy-18-methyl-15α,16α-methylene-2,5(10)-estradien-17α-ol in 10 ml. of dimethyl sulfoxide and 2.8 ml. of triethylamine. After 2 hours, the reaction mixture is introduced into ice water. The thus-precipitated product is vacuum-filtered, washed with water, and dissolved in methylene chloride, yielding 880 mg. of crude 3-methoxy-18-methyl-15α,16α-methylene-2,5(10)-estradien-17-one.

A solution of ethylmagnesium bromide in tetrahydrofuran, produced from 500 mg. of magnesium filings and 1.6 ml. of ethyl bromide, is added dropwise under ice cooling to 28 ml. of absolute tetrahydrofuran, through which is passed acetylene. This solution is combined with 550 mg. of crude 3-methoxy-18-methyl-15α,16α-methylene-2,5(10)-estradien-17-one in 20 ml. of absolute tetrahydrofuran. The mixture is agitated for 2.5 hours at room temperature, then mixed under ice cooling with saturated ammonium chloride solution, and diluted with ether. After drying and removing the solvent by distillation, 600 mg. of crude 17α-ethinyl-3-methoxy-18-methyl-15α,16α-methylene-2,5(10)-estradien-17α-ol is isolated.

400 mg. of crude 17α-ethinyl-3-methoxy-18-methyl-15α,16α-methylene-2,5(10)-estradien-17α-ol is refluxed in 18 ml. of methanol and 3.6 ml. of water with 400 mg. of oxalic acid for 3.5 hours. The solution is then diluted with water; the reaction product is extracted with ether, washed with water, and dried over sodium sulfate. Chromatography of the crude product on silica gel with acetone/hexane yields 290 mg. of 17α-ethinyl-17α-hydroxy-18-methyl-15α,16α-methylene-4-estren-3-one, m.p. 188°–189° C. $[\alpha]_D^{20} = -79°$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17α-oxy-1,3,5(10),15-estratetraene of the formula

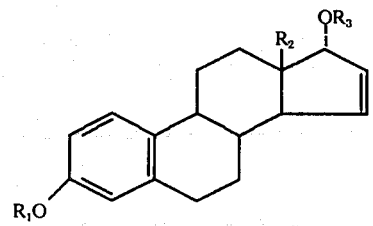

wherein $R_1$ is a hydrogen atom, alkyl of 1–5 carbon atoms or alkanoyl of 1–5 carbon atoms; $R_2$ is ethyl and $R_3$ is a hydrogen atom, alkyl of 1–5 carbon atoms or alkanoyl of 1–5 carbon atoms or tetrahydropyranyl or tetrahydrofuryl.

2. A compound of claim 1, wherein alkanoyl is acetyl.

3. A compound of claim 1, wherein $R_1$ is H, methyl or acetyl and $R_3$ is H or acetyl.

4. A compound of claim 1, 3-methoxy-18-methoxy-18-methyl-17α-tetrahydropyranyloxy-1,3,5(10),15-estratetraene.

5. A compound of claim 1, 3-methoxy-18-methyl-1,3,5(10),15-estratetraene-17α-ol.

6. A compound of claim 1, 17α-acetoxy-3-methoxy-18-methyl-1,3,5(10),15-estratetraene.

7. A compound of claim 1, 3-methoxy-17α-tetrahydropyranyloxy-1,3,5(10),15-estratetraene.

8. A pharmaceutical composition comprising an estrogenically effective amount of a compound of claim 1, in unit dosage form and in admixture with a pharmaceutically acceptable carrier.

9. A process for the production of 17α-hydroxy-1,3,5(10),15-estratetraenes of claim 1, which comprises the steps of heating, in the presence of an alkaline reagent reactive with hydrogen halide, a 16β-halo-17α-tetrahydropyranyloxy estratriene of the formula

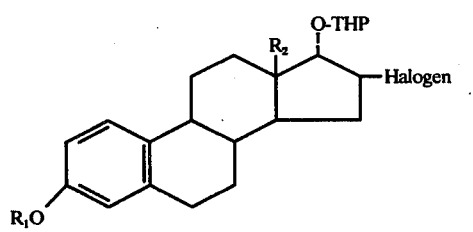

wherein $R_1$ is a hydrogen atom, alkyl of 1–5 carbon atoms or alkanoyl of 1–5 carbon atoms and $R_2$ is alkyl of 1–5 carbon atoms, halogen is chlorine or bromine and THP is tetrahydropyranyl.

10. A process according to claim 9, wherein the starting estratetraene is produced by reacting the corresponding 16α,17α-epoxide with lithium halide or HCl in glacial acetic acid and converting the halohydrin into the 17-tetrahydropyranyl ether by reaction with dihydropyran in the presence of acid.

11. A process for the production of 17α-hydroxy-1,3,5(10),15-estratetraenes of claim 1, which comprises a. reacting a 16α,17α-epoxy-estratriene of the formula

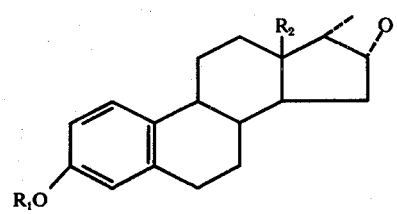

wherein $R_1$ is a hydrogen atom, alkyl of 1–5 carbon atoms or alkanoyl of 1–5 carbon atoms and $R_2$ is alkyl of 1–5 carbon atoms, with diphenyldiselenide to the corresponding selenium oxide of the formula

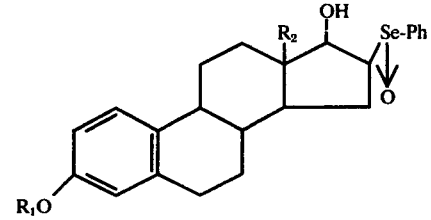

and introducing the $\Delta^{15}$-double bond by heating the thus-produced selenium oxide while splitting off Ph-Se-OH; or b. reacting the starting 16α,17α-epoxy-estratriene with the lithium salt of a strong base.

12. A 16β-halo-17α-tetrahydropyranyloxy estratriene of the formula

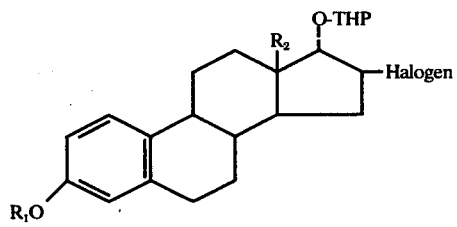

wherein $R_1$ is a hydrogen atom, alkyl of 1–5 carbon atoms or alkanoyl of 1–5 carbon atoms and $R_2$ is alkyl of 1–5 carbon atoms.

13. A 16α,17α-epoxy-estratriene of the formula

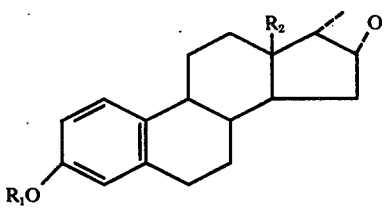

wherein $R_1$ is a hydrogen atom or alkanoyl of 1–5 carbon atoms and $R_2$ is ethyl.

14. A compound of the formula

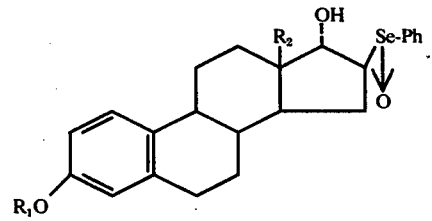

wherein $R_1$ is a hydrogen atom, alkyl of 1–5 carbon atoms or alkanoyl of 1–5 carbon atoms and $R_2$ is alkyl of 1–5 carbon atoms.

15. A 17α-tetrahydropyranyloxy-1,3,5(10),15-estratetraene of the formula

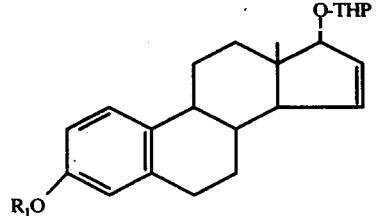

wherein $R_1$ is a hydrogen atom, alkyl of 1–5 carbon atoms or alkanoyl of 1–5 carbon atoms and THP is tetrahydropyranyl.

* * * * *